US009163294B2

(12) United States Patent
Minamino et al.

(10) Patent No.: US 9,163,294 B2
(45) Date of Patent: Oct. 20, 2015

(54) METHOD OF MANUFACTURING SUGAR SOLUTION

(75) Inventors: Atsushi Minamino, Kamakura (JP);
Hiroyuki Kurihara, Kamakura (JP);
Katsushige Yamada, Kamakura (JP)

(73) Assignee: Toray Industries, Inc. (JP)

( * ) Notice: Subject to any disclaimer, the term of this patent is extended or adjusted under 35 U.S.C. 154(b) by 7 days.

(21) Appl. No.: 14/235,943

(22) PCT Filed: Jul. 27, 2012

(86) PCT No.: PCT/JP2012/069137
§ 371 (c)(1),
(2), (4) Date: Jan. 29, 2014

(87) PCT Pub. No.: WO2013/018694
PCT Pub. Date: Feb. 7, 2013

(65) Prior Publication Data
US 2014/0178937 A1    Jun. 26, 2014

(30) Foreign Application Priority Data
Jul. 29, 2011  (JP) .................. 2011-167542

(51) Int. Cl.
C13K 1/04      (2006.01)
C12P 19/14     (2006.01)
C13K 13/00     (2006.01)
C12P 19/02     (2006.01)

(52) U.S. Cl.
CPC . *C13K 1/04* (2013.01); *C12P 19/02* (2013.01); *C12P 19/14* (2013.01); *C13K 13/002* (2013.01)

(58) Field of Classification Search
IPC ........................................... C13K 1/04
See application file for complete search history.

(56) References Cited

U.S. PATENT DOCUMENTS

| | | | | | |
|---|---|---|---|---|---|
| 4,966,850 | A | * | 10/1990 | Yu et al. | ......... 435/200 |
| 5,508,183 | A | * | 4/1996 | Scott et al. | ......... 435/165 |
| 2005/0056600 | A1 | | 3/2005 | Ranney | |
| 2005/0211239 | A1 | | 9/2005 | Koivikko et al. | |
| 2009/0023187 | A1 | | 1/2009 | Foody et al. | |
| 2009/0056889 | A1 | | 3/2009 | Ren et al. | |
| 2011/0201091 | A1 | * | 8/2011 | Dale | ......... 435/244 |

FOREIGN PATENT DOCUMENTS

| | | |
|---|---|---|
| CN | 101787398 A | 7/2010 |
| JP | 11-506934 | 6/1999 |
| JP | 3041380 | 10/2000 |
| JP | 2001-095594 | 10/2001 |

(Continued)

OTHER PUBLICATIONS

Supplementary European Search Report dated Mar. 17, 2015 of corresponding European Application No. 12820603.4.

(Continued)

*Primary Examiner* — Rosanne Kosson
(74) *Attorney, Agent, or Firm* — DLA Piper LLP (US)

(57) ABSTRACT

A method of producing a sugar liquid with a cellulose-containing biomass as a raw material includes (1) hydrolyzing a cellulose-containing biomass to produce an aqueous sugar solution, and (2) filtering the aqueous sugar solution obtain in (1) through an ultrafiltration membrane having a molecular weight cutoff of 600 to 2,000 to remove a fermentation inhibitor(s) into the permeate side and collect a sugar liquid from the feed side.

11 Claims, 4 Drawing Sheets

(56) References Cited

FOREIGN PATENT DOCUMENTS

| | | |
|---|---|---|
| JP | 2005-229821 | 2/2005 |
| JP | 2008-535664 | 4/2008 |
| JP | 2008-161125 | 7/2008 |
| WO | 2009/110374 | 9/2009 |
| WO | 2009/131304 A2 | 10/2009 |
| WO | 2010/067785 | 6/2010 |

OTHER PUBLICATIONS

Benkun Qi, et al., "Separation of furfural from monosaccharides by nanofiltration", *Bioresource Technology*, vol. 102, No. 14, Apr. 16, 2011, p. 7111-7118, (tables 1, 5).

Furuichi, M., "Use of Membrane Separation Technologies in Process for Producing Alcohol from Biomass," *Bioscience & Industry*, Sep. 1, 1989, vol. 47, pp. 951 to 954 (English translation pp. 1-8).

\* cited by examiner

METHOD OF MANUFACTURING SUGAR SOLUTION

TECHNICAL FIELD

This disclosure relates to a method of producing a sugar liquid from a cellulose-containing biomass.

BACKGROUND

The process of fermentation production of chemical products using sugars as raw materials has been used to produce various industrial materials. At present, as the sugars to be used as fermentation feedstocks, those derived from food materials such as sugar cane, starch and sugar beet are industrially used. However, in view of the fact that rise in the prices of food materials is expected due to future increase in the world population, or in an ethical view of the fact that sugars for industrial materials may compete with sugars for food, a process of efficiently producing a sugar liquid from a renewable nonfood resource, that is, cellulose-containing biomass, or a process of using the obtained sugar liquid as a fermentation feedstock to efficiently convert it to an industrial material, needs to be constructed in the future.

As the prior art for obtaining sugar from biomass, methods wherein concentrated sulfuric acid is used to hydrolyze cellulose and hemicellulose contained in the biomass into monosaccharides represented by glucose and xylose (Japanese Translated PCT Patent Application Laid-open No. 11-506934 and JP 2005-229821 A), and methods wherein pretreatment is carried out for improving the reactivity of biomass, followed by hydrolysis of the biomass by enzymatic reaction (JP 2001-95594 A and JP 3041380 B) are generally known. In such cases, in hydrolysis of a cellulose-containing biomass, decomposition of the cellulose and hemicellulose components and the like proceeds while decomposition reaction of produced sugars such as glucose and xylose proceeds, leading to production of by-products such as furan compounds including furfural and hydroxymethylfurfural, and organic acids including formic acid and acetic acid, which is problematic. These compounds have inhibitory actions during the fermentation step using a microorganism and cause inhibition of the growth of the microorganism, leading to a decreased yield of the fermentation product. Therefore, these compounds are called fermentation inhibitors and have been seriously problematic when a sugar liquid derived from a cellulose-containing biomass was used as a fermentation feedstock. As a method of removing such fermentation inhibitors in the sugar liquid production process, a method by removing fermentation inhibitors with a nanofiltration membrane or reverse osmosis membrane is known (WO 2010/067785).

PRIOR ART DOCUMENTS

Patent Documents

Patent Document 1: Japanese Translated PCT Patent Application Laid-open No. 11-506934
Patent Document 2: JP 2005-229821 A
Patent Document 3: JP 2001-95594 A
Patent Document 4: JP 3041380 B
Patent Document 5: WO2010/067785

We discovered that, as described above, the operation of removal of fermentation inhibitors contained in a sugar liquid derived from a cellulose-containing biomass using a nanofiltration membrane or reverse osmosis membrane sometimes results in incomplete removal of the fermentation inhibitors, and assumed that this occurs because unidentified fermentation inhibitors that can be hardly removed with a nanofiltration membrane or reverse osmosis membrane may be contained in a sugar liquid derived from a cellulose-containing biomass. Thus, it could be helpful to provide a method of producing a sugar liquid containing only a very small amount of fermentation inhibitors by removing fermentation inhibitors that have been difficult to remove by conventional methods from a sugar liquid derived from a cellulose-containing biomass.

SUMMARY

We discovered that fermentation inhibitors produced in the step of producing a sugar liquid from a cellulose-containing biomass contain substances having molecular weights equivalent to or higher than those of monosaccharides such as coumaric acid, ferulic acid, coniferyl aldehyde and 2,3-dihydrobenzofuran, and then discovered that these can be efficiently removed with an ultrafiltration membrane.

We thus provide [1] to [6] below:

[1] A method of producing a sugar liquid using a cellulose-containing biomass as a raw material, the method comprising the steps of:
(1) hydrolyzing a cellulose-containing biomass to produce an aqueous sugar solution; and
(2) filtering the aqueous sugar solution obtained in Step (1) through an ultrafiltration membrane having a molecular weight cutoff of 600 to 2,000, to remove a fermentation inhibitor(s) into the permeate side and collect a sugar liquid from the feed side.

[2] The method of producing a sugar liquid according to [1], wherein the fermentation inhibitor(s) comprise(s) one or more substances selected from the group consisting of coumaric acid, ferulic acid and 2,3-dihydrobenzofuran.

[3] The method of producing a sugar liquid according to [1] or [2], wherein, in the Step (2), the aqueous sugar solution is filtered after adjusting the pH to not more than 5.

[4] The method of producing a sugar liquid according to any one of [1] to [3], wherein the material of the functional layer of the ultrafiltration membrane used in the Step (2) is polyethersulfone.

[5] The method of producing a sugar liquid according to any one of [1] to [4], the method comprising filtering the permeate obtained in Step (2) containing a sugar liquid and/or fermentation inhibitor through a nanofiltration membrane and/or reverse osmosis membrane, to collect a concentrated sugar liquid from the feed side.

[6] A method of producing a chemical product, the method comprising using, as a fermentation feedstock, a sugar liquid obtained by the method for producing a sugar liquid according to any one of [1] to [5].

A sugar liquid containing sugars such as glucose and xylose can be produced at high purity and high yield. As a result, by using the obtained purified sugar liquid as a fermentation feedstock, the efficiencies of fermentation production of various chemical products can be improved.

DESCRIPTION OF SYMBOLS

Figure 1:
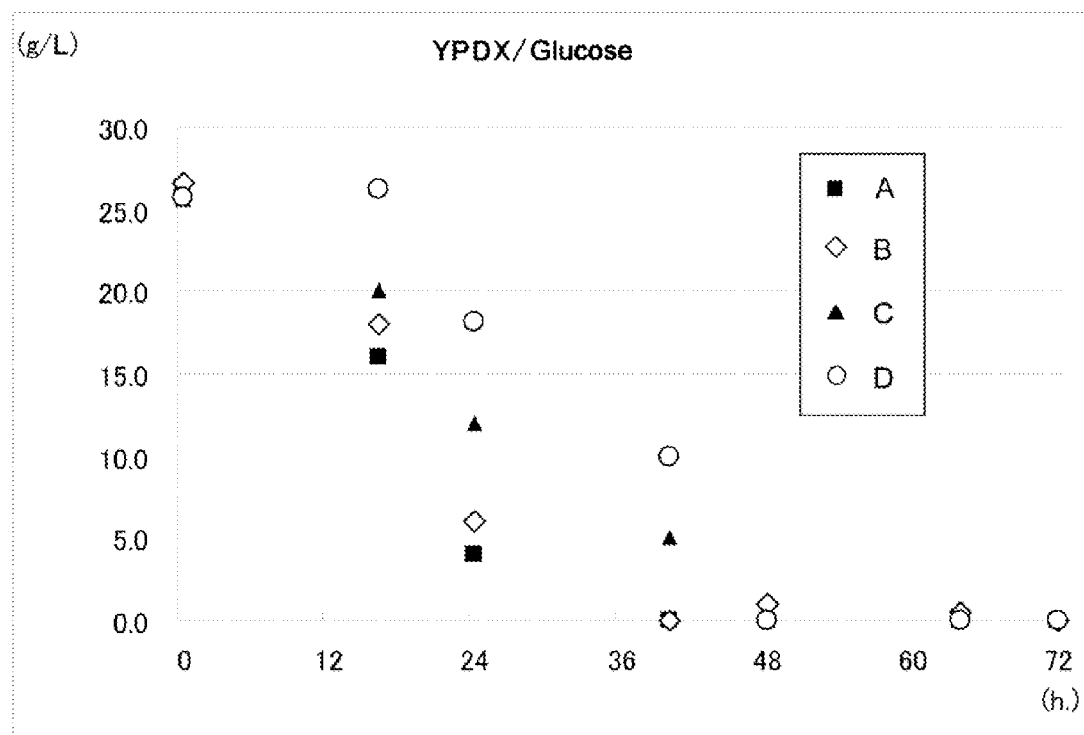
FIG. 1 shows the results of a test for fermentation with a sugar liquid produced by concentrating, using an ultrafiltration membrane or nanofiltration membrane, an aqueous sugar solution obtained by dilute sulfuric acid treatment of a cellulose-containing biomass, which test was carried out using as an index the glucose consumption rate.

A Sugar liquid obtained by filtration treatment of a dilute-sulfuric-acid-treated aqueous sugar solution with an ultrafiltration membrane "NTR-7450."

B Sugar liquid obtained by filtration treatment of a dilute-sulfuric-acid-treated aqueous sugar solution with an ultrafiltration membrane "SPE1."

C Sugar liquid obtained by filtration treatment of a dilute-sulfuric-acid-treated aqueous sugar solution with an ultrafiltration membrane "GR95Pp."

D Sugar liquid obtained by filtration treatment of a dilute-sulfuric-acid-treated aqueous sugar solution with a nanofiltration membrane "UTC-60."

E Sugar liquid obtained by filtration treatment of a steam-explosion-treated aqueous sugar solution with an ultrafiltration membrane "NTR-7450."

F Sugar liquid obtained by filtration treatment of a steam-explosion-treated aqueous sugar solution with an ultrafiltration membrane "SPE1."

G Sugar liquid obtained by filtration treatment of a steam-explosion-treated aqueous sugar solution with an ultrafiltration membrane "GR95Pp."

H Sugar liquid obtained by filtration treatment of a steam-explosion-treated aqueous sugar solution with a nanofiltration membrane "UTC-60."

I Concentrated sugar liquid obtained by filtration treatment of a hydrothermally treated aqueous sugar solution with a nanofiltration membrane "UTC-60."

J Concentrated sugar liquid obtained by filtration treatment of a hydrothermally treated aqueous sugar solution with an ultrafiltration membrane "NTR-7410" followed by filtration treatment of the obtained permeate with a nanofiltration membrane "UTC-60."

K Concentrated sugar liquid obtained by filtration treatment of an aqueous sulfuric acid solution with a nanofiltration membrane "UTC-60."

L Concentrated sugar liquid obtained by filtration treatment of an aqueous sulfuric acid solution with an ultrafiltration membrane "NTR-7450" followed by filtration treatment of the obtained permeate with a nanofiltration membrane "UTC-60."

DETAILED DESCRIPTION

Step (1)

The cellulose-containing biomass means a resource that is derived from an organism and comprises not less than 5% by weight of cellulose. Specific examples of the cellulose-containing biomass include herbaceous biomasses such as bagasse, switchgrass, napier grass, *Erianthus*, corn stover, rice straw and wheat straw; and woody biomasses such as trees and waste building materials. Since such cellulose-containing biomasses contain lignin as aromatic macromolecules in addition to cellulose/hemicellulose, they are also called lignocellulose. By hydrolyzing cellulose and hemicellulose, which are polysaccharide components contained in a cellulose-containing biomass, a sugar liquid containing monosaccharides that can be utilized as a fermentation feedstock for production of a chemical product, more specifically, a sugar liquid containing as major components xylose and glucose, can be obtained.

Specific examples of the hydrolysis treatment of a cellulose-containing biomass include chemical treatments, for example, acid treatment in which treatment is carried out with dilute sulfuric acid, a sulfite or the like at high temperature and high pressure; alkali treatment in which treatment is carried out with an aqueous solution of an alkali such as calcium hydroxide or sodium hydroxide; ammonia treatment in which treatment is carried out with liquid ammonia, ammonia gas or an aqueous ammonia solution; and hydrothermal treatment in which treatment is carried out with pressurized hot water. These hydrolysis treatments may be further combined with hydrolysis treatment with a saccharifying enzyme.

In general, lignin is dissolved in the acid treatment. Further, the hemicellulose component, which has low crystallinity, is first hydrolyzed, followed by degradation of the cellulose component, which has high crystallinity. Therefore, a liquid containing a larger amount of xylose derived from hemicellulose can be obtained. The number of times of the treatment is not limited and, by setting two or more stages of the acid treatment process, hydrolysis conditions suitable for hemicellulose or cellulose can be selectively set, and an increased degradation efficiency and sugar yield can hence be achieved. The acid used in the acid treatment is not limited as long as the acid causes hydrolysis, and sulfuric acid is preferred from an economic point of view. The concentration of the acid is preferably 0.1 to 100% by weight, more preferably 0.5 to 15% by weight. The reaction temperature may be 100 to 300° C., and the reaction time can be 1 second to 60 minutes. The liquid component obtained after the acid treatment comprises a large amount of monosaccharides and their oligosaccharides obtained by hydrolysis, mainly containing components derived from hemicellulose. In particular, the hydrolysis can be achieved in a single stage by utilizing the action of concentrated sulfuric acid at a concentration of not less than 50%, more preferably not less than 80%, to hydrolyze both hemicellulose and cellulose. In cases where the acid treatment is followed by hydrolysis with a saccharifying enzyme, the solid content and the liquid component obtained after the acid treatment may be separately subjected to the hydrolysis with a saccharifying enzyme, or the mixture of the solid content and the liquid component may be subjected to the hydrolysis without separation. Since the solid content and the liquid component obtained by the acid treatment contain the acid employed, the acid-treated product is preferably neutralized before performing the hydrolysis reaction using a saccharifying enzyme.

The alkali treatment is a treatment method in which a cellulose-containing biomass is reacted in an aqueous alkaline solution, more specifically, an aqueous solution of a hydroxide salt (excluding ammonium hydroxide). By the alkali treatment, lignin, which mainly inhibits the reaction of cellulose/hemicellulose caused by the saccharification enzyme, can be removed. As the hydroxide salt, sodium hydroxide or calcium hydroxide is preferably used. The concentration of the alkali in the aqueous solution is preferably 0.1 to 60% by weight. This solution is added to the cellulose-containing biomass, and the treatment is carried out usually at a temperature 100 to 200° C., preferably 110 to 180° C. The number of times of treatment is not limited, and the treatment may be carried out one or more times. In cases where the treatment is carried out 2 or more times, the conditions for the plurality of times of treatment may be different from each other. Since the pretreated product obtained by the alkali treatment contains an alkali, the pretreated product is preferably neutralized before the hydrolysis with a saccharifying enzyme.

The ammonia treatment is a treatment method in which an aqueous ammonia solution or 100% ammonia (liquid or gas) is reacted with a cellulose-derived biomass and, for example, the method described in JP 2008-161125 A or JP 2008-535664 A may be employed. It is said that, in the ammonia treatment, ammonia reacts with the cellulose component to break the crystallinity of cellulose, leading to a remarkable increase in the efficiency of reaction by the saccharifying enzyme. Ammonia is usually added to the cellulose-containing biomass such that the ammonia concentration is 0.1 to 15% by weight with respect to the cellulose-containing biomass, and the treatment is carried out at 4° C. to 200° C., preferably 60° C. to 150° C. The number of times of treatment is not limited, and the treatment may be carried out one or more times. In cases where the pretreated product obtained by the ammonia treatment is further subjected to hydrolysis using a saccharifying enzyme, it is preferred to carry out neutralization of ammonia or removal of ammonia in advance.

The hydrothermal treatment is a treatment method in which a cellulose-derived biomass is treated with pressurized hot water at a temperature of 100 to 400° C. for 1 second to 60 minutes. The treatment is usually carried out such that the cellulose-containing biomass after the treatment, which is insoluble in water at a normal temperature of 25° C., is contained at a concentration of 0.1 to 50% by weight with respect to the total weight of the cellulose-containing biomass and water. The pressure is not limited since it depends on the processing temperature, and is preferably 0.01 to 10 MPa. In the hydrothermal treatment, the components eluted into the hot water vary depending on the temperature of the pressurized hot water. In general, as the temperature of the pressurized hot water increases, elution of tannin and lignin as the first group from the cellulose-containing biomass occurs first, and elution of hemicellulose as the second group then occurs at a temperature of not less than 140 to 150° C., further followed by elution of cellulose as the third group at a temperature higher than about 230° C. Further, at the same time as the elution, hydrolysis of hemicellulose and cellulose may occur. The difference in the eluted components depending on the temperature of the pressurized hot water may be utilized to increase the reaction efficiencies of the saccharifying enzyme for cellulose and hemicellulose, by performing a multi-stage treatment at different temperatures. Among the fractions obtained by the hydrothermal treatment, the water-soluble matter containing the components eluted into the pressurized hot water is referred to as the hot-water-soluble matter, and the components other than the hot-water-soluble matter are referred to as the hot-water-insoluble matter.

The hot-water-insoluble matter is solid matter obtained as a result of elution of large amounts of lignin and the hemicellulose component, and mainly contains di- and higher saccharides as the cellulose (C6) component. In addition to cellulose as the main component, the hot-water-insoluble matter may contain the hemicellulose component and the lignin component. The ratios of contents of these components may vary depending on the temperature of the pressurized hot water during the hydrothermal treatment and on the type of the biomass to be processed. The water content in the hot-water-insoluble matter is 10% to 90%, more preferably 20% to 80%.

The hot-water-soluble matter is a water-soluble matter in the liquid state or slurry state, and contains hemicellulose, lignin, tannin and a part of the cellulose component eluted into the pressurized hot water in the liquid state or slurry state. The hot-water-soluble matter contains a large amount of polysaccharides, oligosaccharides and monosaccharides produced by hydrolysis. These may be used, as it is or after additional hydrolysis with a saccharifying enzyme, as the aqueous sugar solution.

A pretreatment(s) may be carried out before performing the hydrolysis treatment method, and examples of the pretreatment(s) include pulverization treatment in which fibers are mechanically cut using a cutter mill, hammer mill or the like; fine pulverization treatment in which a ball mill or jet mill is used; wet treatment in which a grinder is used; mechanochemical treatment; and steam explosion treatment in which a cellulose-containing biomass is steamed with water vapor for a short time and the pressure is then instantaneously released to cause pulverization due to volume expansion. This is because pulverization increases the exposed area of cellulose/hemicellulose, and hence enhances the efficiency of hydrolysis with a saccharifying enzyme.

The saccharifying enzyme is not limited as long as the enzyme has a cellulose- or hemicellulose-degrading activity, and is preferably a saccharifying enzyme produced by a filamentous fungus belonging to the genus *Trichoderma*. *Trichoderma* filamentous fungi are microorganisms that extracellularly secrete many kinds of saccharifying enzymes, and the saccharifying enzyme is preferably derived from *Trichoderma reesei*. Further, in addition to an enzyme having a cellulose- or hemicellulose-degrading activity, an enzyme that supports degradation of cellulose or hemicellulose is also preferably contained. Examples of the enzyme that supports degradation of cellulose or hemicellulose include cellobiohydrolase, endoglucanase, exoglucanase, β-glucosidase, xylanase and xylosidase, and biomass-swelling enzymes. The hydrolysis reaction using a saccharifying enzyme is carried out preferably at a pH of about 3 to 7, more preferably at a pH of about 5. The reaction temperature is preferably 40 to 70° C. Further, the hydrolysis with an enzyme is preferably followed by solid-liquid separation to remove undegraded solids. Examples of the method of removal of solids include, but are not limited to, centrifugation and membrane separation. A plurality of these solid-liquid separation methods may be used in combination.

To prevent clogging or fouling of the ultrafiltration membrane in Step (2), the aqueous sugar solution obtained in Step (1) is preferably subjected to removal of solids, and water-soluble macromolecules such as oligosaccharides, polysaccharides, tannin, saccharifying enzyme and biomass-derived protein components before subjecting the solution to Step (2). The method of removing these components is not limited, and preferred examples of the removal method include a method in which the aqueous sugar solution is filtered through a microfiltration membrane, and/or an ultrafiltration membrane having a molecular weight cutoff of larger than 2,000, to remove solids and water-soluble macromolecules into the feed side. The removal is preferred. Examples of the method of filtration include, but are not limited to, pressure filtration, vacuum filtration and centrifugal filtration. The filtration operation is not limited, and can be roughly classified into constant pressure filtration, constant flow filtration and variable pressure/variable flow filtration. The filtration operation may be multi-stage filtration in which a microfiltration membrane(s), and/or ultrafiltration membrane(s) having a molecular weight cutoff of larger than 2,000, is/are used two or more times for efficient removal of solids.

The microfiltration membrane means a membrane having an average pore size of 0.01 μm to 5 mm, which is called MF membrane or the like for short, and the membrane is preferably used when solids contained in the aqueous sugar solution are to be removed. The microfiltration membrane used herein may be either an inorganic membrane or organic membrane, and examples of the material of the membrane include organic materials such as cellulose, cellulose ester, polysulfone, polyethersulfone, chlorinated polyethylene, polypropylene, polyolefin, polyvinyl alcohol, polymethyl methacrylate, polyvinylidene fluoride and polytetrafluoroethylene; and inorganic materials such as metals including stainless steel, and ceramics.

The ultrafiltration membrane is the one described in detail in the Step (2) below, and use of an ultrafiltration membrane having a molecular weight cutoff of more than 2,000 is preferred to remove water-soluble macromolecules, especially the saccharifying enzyme, contained in the aqueous sugar solution.

Step (2)

It is known that, when a cellulose-containing biomass is hydrolyzed in Step (1), fermentation inhibitors are produced in addition to sugars. Fermentation inhibitors are compounds produced by hydrolysis of a cellulose-containing biomass, and are substances having an action to cause reduction in the amount of a chemical product produced or accumulated, or in the production rate, in the fermentation process for production of a chemical product using a sugar liquid as a raw material. The extent of fermentation inhibition by the fermentation inhibitors is not limited since the extent of inhibition of the microorganism varies depending on the types and amounts of fermentation inhibitors present in the aqueous sugar solution, on the species of the microorganism employed, and on the type of the chemical product to be produced.

Organic acids such as acetic acid and formic acid; furan compounds such as furfural and hydroxymethylfurfural (HMF); and phenol compounds such as vanillin and 4-hydroxybenzoic acid; have been known as fermentation inhibitors so far, but we discovered that coumaric acid, ferulic acid, 2,3-dihydrobenzofuran and the like, in addition to those known fermentation inhibitors, can be fermentation inhibitors. In Step (2), the aqueous sugar solution obtained in Step (1) is filtered through an ultrafiltration membrane having a specific molecular weight cut off to remove fermentation inhibitors into the permeate side, while a sugar liquid is recovered from the feed side.

The ultrafiltration membrane is a separation membrane having a molecular weight cutoff of 600 to 200,000, which is also called UF membrane or the like for short. The molecular weight cutoff is well known as an index indicating a membrane performance of an ultrafiltration membrane, as is described in p. 92 of The Membrane Society of Japan ed., Membrane Experiment Series, Vol. III, Artificial Membrane, editorial committee members: Shoji Kimura, Shin-ichi Nakao, Haruhiko Ohya and Tsutomu Nakagawa (1993, Kyoritsu Shuppan Co., Ltd.), that "The curve obtained by plotting the molecular weight of the solute along the abscissa and the blocking rate along the ordinate is called the molecular weight cutoff curve. The molecular weight with which the blocking rate reaches 90% is called the molecular weight cutoff of the membrane." In the technical field of separation membranes, a separation membrane having a molecular weight cutoff of 600 to 1,000 is recognized as a membrane on the borderline between a nanofiltration membrane and an ultrafiltration membrane. Therefore, a separation membrane having a molecular weight cutoff of 600 to 1,000 is called a nanofiltration membrane or an ultrafiltration membrane depending on the literature. Thus, a separation membrane having a molecular weight cutoff of 600 to 200,000 is called an ultrafiltration membrane, and a separation membrane that has a molecular weight cutoff of less than 600 and corresponds to a membrane generally defined as "a membrane that allows permeation of monovalent ions but blocks divalent ions" is called a nanofiltration membrane.

We use ultrafiltration membranes having a molecular weight cutoff of 600 to 2,000. Use of an ultrafiltration membrane having a molecular weight cutoff of more than 2,000 is not preferred since it causes permeation of both most of sugars and fermentation inhibitors into the permeate side, and use of a membrane having a molecular weight cutoff of less than 600 is not preferred since it leads to a low performance of removal of the newly identified fermentation inhibitors, that is, coumaric acid, ferulic acid and 2,3-dihydrobenzofuran, into the permeate side.

Examples of the material of the ultrafiltration membrane include, but are not limited to, organic materials such as cellulose, cellulose ester, polysulfone, sulfonated polysulfone, polyethersulfone, sulfonated polyethersulfone, chlorinated polyethylene, polypropylene, polyolefin, polyvinyl alcohol, polymethyl methacrylate, polyvinylidene fluoride and polytetrafluoroethylene; metals such as stainless steel; and inorganic materials such as ceramics. An organic membrane is especially preferred from the viewpoint of the removal performance for hydrophobic substances. In particular, polyethersulfone is preferred. This is because a polyethersulfone membrane was found to have a good performance for separation of sugars of interest from fermentation inhibitors. The material is more preferably a sulfonated polyethersulfone. This is because sulfonated polyethersulfone has a higher blocking rate for sugars than unsulfonated polyethersulfone.

The form of the ultrafiltration membrane is not limited, and may be any of a spiral type, hollow fiber type, tubular type and flat membrane type.

Specific examples of the ultrafiltration membrane used in the present invention include the G-5 type, GH type and GK type, manufactured by DESAL; SPE1, manufactured by Synder; PM1000, PM2000, MPS-36 and SR2, manufactured by KOCH; GR95Pp and ETNA01PP, manufactured by Alfa-Laval; and NTR-7450 (molecular weight cutoff, 600 to 800; see WaterResearch 37 (2003) 864-872) and NTR-7410 (molecular weight cutoff, 1,000 to 2,000; see Collection of Papers for Sanitary Engineering Symposium, 5:246-251 (1997)), manufactured by Nitto Denko Corporation.

The filtration pressure in the filtration treatment with the ultrafiltration membrane is preferably 0.1 MPa to 8 MPa, although the filtration pressure varies depending on the concentration of the aqueous sugar solution. In cases where the filtration pressure is lower than 0.1 MPa, the membrane permeation rate is low, while in cases where the filtration pressure is higher than 8 MPa, the membrane may be damaged. In cases where the filtration pressure is 0.5 MPa to 6 MPa, the membrane permeation flux is high and efficient permeation of the sugar solution is therefore possible, which is more preferred.

The membrane permeation flux in the filtration treatment with the ultrafiltration membrane is preferably 0.2 m/D to 24.0 m/D. This is because a membrane permeation flux of not more than 0.2 m/D does not allow concentration with an ultrafiltration membrane, and a membrane permeation flux of not more than 2.0 m/D causes remarkable fouling of the membrane. A filtration permeation flux of 0.5 m/D to 2.0 m/D easily allows filtration with the ultrafiltration membrane, which is more preferred.

The pH of the aqueous sugar solution in the filtration treatment with the ultrafiltration membrane is not limited and, in view of the permeability to fermentation inhibitors, the pH is preferably not more than 5, more preferably not more than 4. Since, in cases where the pH is not more than 1, a large amount of acid is required for pH adjustment, the lower limit of the pH is preferably 1 from an economic point of view. The effect of pH adjustment of the aqueous sugar solution is remarkable especially in cases where a substance such as coumaric acid or ferulic acid, which is an aromatic compound having a carboxylic group, is contained as a fermentation inhibitor.

The sugar liquid recovered from the feed side in the filtration treatment with an ultrafiltration membrane may be used as it is as a raw material in the later-described fermentation step, or the sugar solution may be further subjected to the filtration treatment described in WO2010/067785 using a nanofiltration membrane and/or reverse osmosis membrane to concentrate sugars in the feed side, followed by using the resulting concentrated sugar liquid in the later-described fermentation step.

In the filtration treatment with an ultrafiltration membrane, sugars may be partially missed into the permeate side, and, in such a case, the permeate recovered from the permeate side, containing fermentation inhibitors, may be subjected to the filtration treatment described in WO2010/067785 using a nanofiltration membrane and/or reverse osmosis membrane, to recover a concentrated sugar liquid from the retentate side. The concentrated sugar liquid obtained by this process is also used as the raw material in the later-described fermentation step. It should be noted that the concentrated sugar liquid obtained by filtration treatment with a nanofiltration membrane and/or reverse osmosis membrane was also found to show a tendency to have higher fermentation performance in the later-described fermentation step in cases where filtration treatment is carried out with an ultrafiltration membrane having a molecular weight cutoff of 600 to 2,000, compared to cases where filtration treatment is not carried out or cases where filtration treatment is carried out with an ultrafiltration membrane having a molecular weight cutoff higher than 2,000. We believe that this is because an aqueous sugar solution derived from a cellulose-containing biomass contains a small amount of unknown fermentation inhibitors having molecular weights of about 2,000, and that such inhibitors are concentrated with the nanofiltration membrane and/or reverse osmosis membrane.

Fermentation Step

The sugar liquid obtained in Step (2) comprises glucose and/or xylose as a carbon source(s) for the growth of microorganisms and cultured cells that can produce chemical products as metabolites, while the contents of fermentation inhibitors such as coumaric acid, ferulic acid and 2,3-dihydrobenzofuran are very small, so that the sugar liquid can be effectively used as a fermentation feedstock, especially as a carbon source, for production of a chemical product. The fermentation step can be carried out according to the fermentation step described in WO2010/067785.

The chemical product produced by the fermentation step is not restricted as long as it is a substance produced in a culture liquid by the above microorganism or cells. Specific examples of the chemical product include alcohols, organic acids, amino acids and nucleic acids, which are substances mass-produced in the fermentation industry. Examples the alcohols include ethanol, butanol, 1,3-propanediol, 2,3-butanediol, 1,4-butanediol and glycerol; examples of the organic acids include acetic acid, lactic acid, pyruvic acid, succinic acid, malic acid, itaconic acid and citric acid; examples of the nucleic acids include nucleosides such as inosine and guanosine, and nucleotides such as inosinic acid and guanylic acid; and diamine compounds such as cadaverine. Further, our methods may also be applied to production of substances such as enzymes, antibiotics and recombinant proteins.

EXAMPLES

Reference Example 1

Method of Measuring Monosaccharide Concentrations

Concentrations of monosaccharides (glucose concentration and xylose concentration) contained in the sugar liquid obtained in each of the Examples and Comparative Examples were analyzed by HPLC under the following conditions, and quantified based on comparison with standard samples.
Column: Luna $NH_2$ (manufactured by Phenomenex, Inc.)
Mobile phase: Ultrapure water:acetonitrile=25:75 (flow rate, 0.6 mL/min.)
Reaction liquid: None
Detection method: RI (differential refractive index)
Temperature: 30° C.

Reference Example 2

Method of Measuring Concentrations of Fermentation Inhibitors

The concentrations of furan-based fermentation inhibitors (HMF and furfural) and phenol-based fermentation inhibitors (coumaric acid, ferulic acid and 2,3-dihydrobenzofuran), among fermentation inhibitors contained in the sugar liquid, were analyzed by HPLC under the following conditions, and quantified based on comparison with standard samples.
Column: Synergi HidroRP 4.6 mm×250 mm (manufactured by Phenomenex, Inc.)
Mobile phase: Acetonitrile—0.1 wt % $H_3PO_4$ (flow rate, 1.0 mL/min.)
Detection method: UV (283 nm)
Temperature: 40° C.

Organic acids (acetic acid and formic acid), among fermentation inhibitors contained in the sugar liquid, were analyzed by HPLC under the following conditions, and quantified based on comparison with standard samples.
Column: Shim-Pack SPR-H and Shim-Pack SCR101H (manufactured by Shimadzu Corporation) that were linearly arranged
Mobile phase: 5 mM p-Toluenesulfonic acid (flow rate, 0.8 mL/min.)
Reaction liquid: 5 mM p-Toluenesulfonic acid, 20 mM Bis-Tris, 0.1 mM EDTA-2Na (flow rate, 0.8 mL/min.)

Detection method: Electric conductivity
Temperature: 45° C.

Reference Example 3

Step of Hydrolysis of Cellulose-containing Biomass by Dilute Sulfuric Acid Treatment/Enzyme Treatment As the cellulose-containing biomass, rice straw was used. The cellulose-containing biomass was soaked in 1% aqueous sulfuric acid solution, and processed using an autoclave (manufactured by Nitto Koatsu Co., Ltd.) at 150° C. for 30 minutes. Thereafter, solid-liquid separation was carried out to separate sulfuric acid-treated cellulose from the aqueous sulfuric acid solution. Subsequently, the sulfuric acid-treated cellulose was mixed with the dilute-sulfuric-acid treatment liquid with stirring such that the concentration of solids was 10% by weight, and the pH was adjusted to about 5 with sodium hydroxide. To this mixture, "Accellerase Duet" (manufactured by Danisco Japan), which is a saccharifying enzyme derived from *Trichoderma reesei*, was added as the saccharifying enzyme. The resulting mixture was mixed by stirring at 50° C. for 1 day to perform hydrolysis reaction. Thereafter, centrifugation (3000 G) was performed to separate and remove undegraded cellulose and lignin, to obtain a dilute-sulfuric-acid-treated aqueous sugar solution. The compositions of fermentation inhibitors and monosaccharides contained in the dilute-sulfuric-acid-treated aqueous sugar solution were as shown in Tables 1 to 3.

TABLE 1

Quantification of Fermentation Inhibitors 1

| | Formic acid | Acetic acid | HMF | Unit [g/L] Furfural |
|---|---|---|---|---|
| Dilute-sulfuric-acid-treated aqueous sugar solution | 0.1 | 2.4 | 0.125 | 0.875 |

TABLE 2

Quantification of Fermentation Inhibitors 2

| | Coumaric acid | Ferulic acid | Unit [g/L] 2,3-Dihydrobenzofuran |
|---|---|---|---|
| Dilute-sulfuric-acid-treated aqueous sugar solution | 0.15 | 0.075 | 0.01 |

TABLE 3

Quantification of Monosaccharides

| | Glucose | Unit [g/L] Xylose |
|---|---|---|
| Dilute-sulfuric-acid-treated aqueous sugar solution | 25 | 12 |

Reference Example 4

Step of Hydrolysis of Cellulose-containing Biomass by Steam Explosion Treatment/Enzyme Treatment As the cellulose-containing biomass, rice straw was used. To a 2-L steam explosion tester (Nihon Dennetsu Co., Ltd.), 100 g of the cellulose-containing biomass was fed, and steam was then injected thereto. The pressure was kept at 2.5 MPa for 2.5 minutes, and the atmosphere in the container was then released at once to perform explosion treatment, followed by recovering the sample. The temperature inside the container was 225° C. at this time. The water content of the processed product was 84.4%. Water was added to the product such that the solid concentration was 10% by weight, and 1 N aqueous sodium hydroxide solution was added to the resulting mixture to adjust the pH to 5.0. Thereafter, as the saccharifying enzyme, "Accellerase Duet" was added to the mixture, and the resulting mixture was left to stand at 50° C. for 1 day to allow the reaction to proceed. The composition of the obtained aqueous sugar solution is shown in Tables 4 to 6.

TABLE 4

Quantification of Fermentation inhibitors 1

| | Formic acid | Acetic acid | HMF | Unit [g/L] Furfural |
|---|---|---|---|---|
| Steam-explosion-treated aqueous sugar solution | 1.7 | 2.3 | 0.29 | 0.24 |

TABLE 5

Quantification of Fermentation inhibitors 2

| | Coumaric acid | Ferulic acid | Unit [g/L] 2,3-Dihydrobenzofuran |
|---|---|---|---|
| Steam-explosion-treated aqueous sugar solution | 0.15 | 0.11 | 0.08 |

TABLE 6

Quantification of Monosaccharides

| | Glucose | Unit [g/L] Xylose |
|---|---|---|
| Steam-explosion-treated aqueous sugar solution | 34 | 5 |

Reference Example 5

Step of Hydrolysis of Cellulose-containing Biomass by Ammonia Treatment/Enzyme Treatment As the cellulose-containing biomass, rice straw was used. The cellulose-containing biomass was fed to a compact reactor (manufactured by Taiatsu Techno Corporation, TVS-N2 30 mL), and cooled with liquid nitrogen. Into this reactor, ammonia gas at a concentration of 100% was flown, and the sample was completely soaked in 100% liquid ammonia. The lid of the reactor was closed, and the reactor was left to stand at room temperature for about 15 minutes. Subsequently, the reactor was processed in an oil bath at 150° C. for 1 hour. Thereafter, the reactor was removed from the oil bath, and the ammonia gas was immediately leaked in a fume hood, followed by vacuuming the inside of the reactor to 10 Pa with a vacuum pump, thereby drying the cellulose-containing biomass. The processed cellulose-containing biomass was mixed with pure water by stirring such that the solid concentration was 15% by weight, and the pH was adjusted to about 5 with sulfuric acid. To this mixture, "Accellerase Duet" was added as the saccharifying enzyme, and hydrolysis reaction was carried out with stirring at 50° C. for 3 days. Thereafter, centrifugation (3000 G) was performed to separate and remove undegraded cellulose and lignin, to obtain an aqueous sugar solution from which undegraded cellulose and lignin had been removed. The compositions of fermentation inhibitors and monosaccharides contained in the aqueous sugar solution were as shown in Tables 7 to 9.

TABLE 7

Quantification of Fermentation Inhibitors 1

|  | Formic acid | Acetic acid | HMF | Unit [g/L] Furfural |
|---|---|---|---|---|
| Ammonia-treated aqueous sugar solution | 1.1 | 0.5 | 0.012 | 0.005 |

TABLE 8

Quantification of Fermentation Inhibitors 2

|  | Coumaric acid | Ferulic acid | Unit [g/L] 2,3-Dihydrobenzofuran |
|---|---|---|---|
| Ammonia-treated aqueous sugar Solution | 0.03 | 0.008 | 0.005 |

TABLE 9

Quantification of Monosaccharides

|  | Glucose | Unit [g/L] Xylose |
|---|---|---|
| Ammonia-treated aqueous sugar solution | 40 | 24 |

Reference Example 6

Step of Hydrolysis of Cellulose-containing Biomass by Hydrothermal Treatment/Enzyme Treatment As the cellulose-containing biomass, rice straw was used. The cellulose-containing biomass was soaked in water, and processed using an autoclave (manufactured by Nitto Koatsu Co., Ltd.) at 180° C. for 20 minutes. The pressure at this time was 10 MPa. Thereafter, centrifugation (3000 G) was carried out for the solution component and the processed biomass component, to perform solid-liquid separation. The pH of the solution component was 4.0. Thereafter, the pH of the solution component was adjusted to 5.0 with sodium hydroxide. As the saccharifying enzyme, "Accellerase Duet" was added to the mixture, and the resulting mixture was mixed by stirring at 50° C. for 1 day to perform hydrolysis reaction, to obtain a hydrothermally treated liquid. The compositions of fermentation inhibitors and monosaccharides contained in the hydrothermally treated liquid were as shown in Tables 10 to 12.

TABLE 10

Quantification of Fermentation Inhibitors 1

|  | Formic acid | Acetic acid | HMF | Unit [g/L] Furfural |
|---|---|---|---|---|
| Hydrothermally treated liquid | 1.1 | 2.2 | 0.12 | 0.5 |

TABLE 11

Quantification of Fermentation Inhibitors 2

|  | Coumaric acid | Ferulic acid | Unit [g/L] 2,3-Dihydrobenzofuran |
|---|---|---|---|
| Hydrothermally treated liquid | 0.2 | 0.13 | 0.03 |

TABLE 12

Quantification of Monosaccharides

|  | Glucose | Unit [g/L] Xylose |
|---|---|---|
| Hydrothermally treated liquid | 7 | 15 |

Reference Example 7

Method of Evaluation of Fermentation

Using a yeast strain (*Pichia stipitis*, NBRC1687), a fermentation test was carried out. A medium to be used for the fermentation was prepared by dilution to a glucose concentration of 25 g/L and addition of additives to the resulting dilution such that the composition shown in Table 13 was attained, followed by filter sterilization (Millipore, Stericup 0.22 μm). The culture was performed by inoculating the yeast in an amount of 0.5%, and shaking the flask at 150 rpm at 28° C. for 72 hours. The degree of fermentation inhibition was evaluated based on the glucose consumption rate of the yeast strain. The method of evaluation of the glucose consumption rate of the yeast strain was as follows: the medium component was removed in a clean bench under sterile conditions at Hour 16, 24, 40, 48, 64 and 72 after the beginning of the culture, and the medium was centrifuged and filtered, followed by quantifying the glucose concentration by HPLC according to Reference Example 1.

| Composition | Concentration of Composition |
|---|---|
| Glucose | 25 g/L |
| Bacto Yeast Extract | 10 g/L |
| Peptone | 20 g/L |

Example 1

The dilute-sulfuric-acid-treated aqueous sugar solution described in Reference Example 3 was filtered through a microfiltration membrane with a pore size of 0.08 μm, and the permeate from the microfiltration membrane was filtered through an ultrafiltration membrane. As the ultrafiltration membrane, "NTR-7450" (manufactured by Nitto Denko Corporation; material: sulfonated polyethersulfone, molecular weight cutoff: 600 to 800), "NTR-7410" (manufactured by Nitto Denko Corporation; material: sulfonated polyethersulfone, molecular weight cutoff: 1,000), "SPE1" (manufactured by Synder; material: polyethersulfone; molecular weight cutoff: 1,000), GH series manufactured by GE Osmonics (material: polyethylene glycol; molecular weight cutoff; 1,000), "GR95Pp" (manufactured by Alfa-Laval; material: polyethersulfone; molecular weight cutoff: 2,000), or GK series manufactured by GE (material: polyethylene glycol; molecular weight cutoff: 2,000) was used. For each membrane, 1.5 L of the permeate obtained by filtration of the dilute-sulfuric-acid-treated saccharified liquid through the microfiltration membrane was provided, and filtration treatment was carried out using a flat membrane filtration unit "SEPA-II" (manufactured by GE Osmonics) at a membrane surface linear velocity of 20 cm/second and a filtration pressure of 3 MPa until the volume of the liquid collected from the feed side was 0.5 L. The results are shown in Table 14. As a result, it was found that monosaccharides are concentrated by ultrafiltration membrane treatment, but that formic acid, acetic acid, HMF and furfural, which are low-molecular-weight substances, are not concentrated, and moreover, that coumaric acid, ferulic acid and 2,3-dihydrobenzofuran are hardly concentrated. Some of the sugar liquids collected from the feed side of the ultrafiltration membranes were selected (A to C), and subjected to a fermentation test under the conditions of Reference Example 7. The results are shown in FIG. 1.

Comparative Example 1

The same filtration treatment as in Example 1 was carried out using an ultrafiltration membrane having a higher molecular weight cutoff, "SPE3" (manufactured by Synder; material: polyethersulfone; molecular weight cutoff: 3,000), or a nanofiltration membrane "UTC-60" (manufactured by Toray Industries, Inc.; material: piperazine polyamide), HL series (manufactured by GE Osmonics; material: composite membrane) or DK series (manufactured by GE Osmonics; material: composite membrane). The results are shown in Table 14. It was found that use of the ultrafiltration membrane with a molecular weight cutoff of 3,000 results in an extreme decrease in the rate of concentration of monosaccharides. In terms of concentration with the nanofiltration membranes, coumaric acid, ferulic acid and 2,3-dihydrobenzofuran were concentrated although the concentration of the concentrate somewhat varied, and, also in the fermentation test (D), the glucose consumption rate was lower than in the cases of Example 1, in which ultrafiltration membranes (A to C) were used.

Example 2

Figure 2:
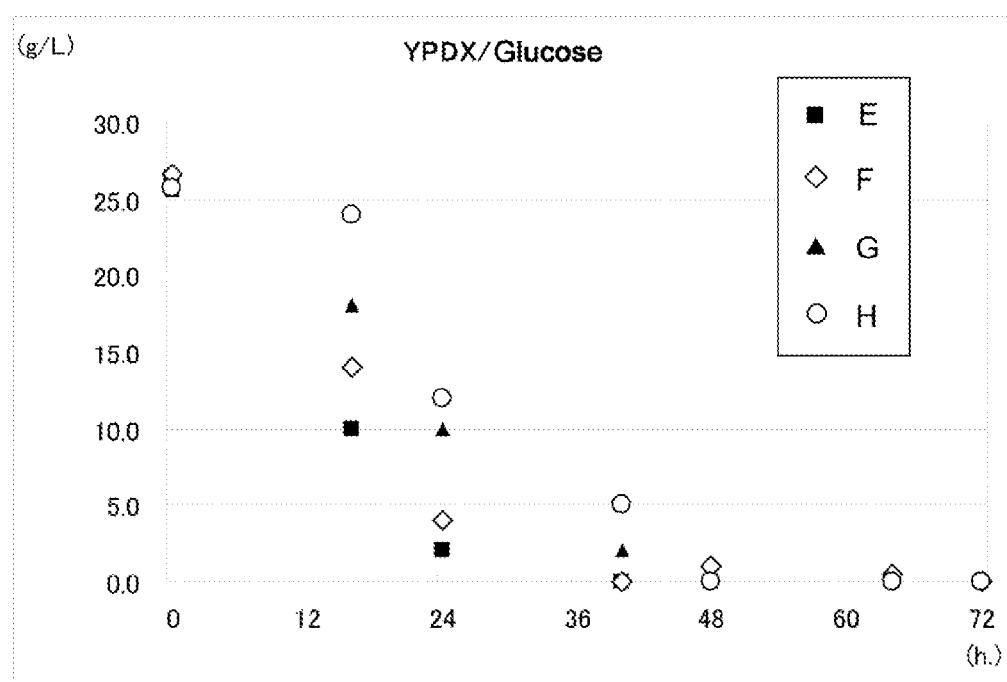
FIG. 2 shows the results of a test for fermentation with a sugar liquid produced by concentrating, using an ultrafiltration membrane or nanofiltration membrane, an aqueous sugar solution obtained by steam explosion treatment of a cellulose-containing biomass, which test was carried out using as an index the glucose consumption rate.

The same filtration treatment as in Example 1 was carried out for the permeate obtained by filtration of the steam-explosion-treated aqueous sugar solution described in Reference Example 4 through the microfiltration membrane. The results are shown in Table 15. Further, the results of fermentation carried out by the method of Reference Example 7 (E to G) are shown in FIG. 2.

Comparative Example 2

The permeate obtained by filtration of the steam-explosion-treated saccharified liquid through a microfiltration membrane was subjected to filtration treatment using the same membranes as in Comparative Example 1. The results on the liquid composition are shown in Table 15, and the results of the fermentation test are shown in FIG. 2. Similarly to the results of comparison between Example 1 and Comparative Example 1, use of the ultrafiltration membrane with a molecular weight cutoff of 3,000 resulted in an extreme decrease in the rate of concentration of monosaccharides. In terms of concentration with the nanofiltration membranes, coumaric acid, ferulic acid and 2,3-dihydrobenzofuran were concentrated although the concentration of the concentrate somewhat varied, and, also in the fermentation test (H), the glucose consumption rate was lower than in the cases of Example 2, in which ultrafiltration membranes were used.

TABLE 14

Filtration Treatment of Dilute-sulfuric-acid-treated Aqueous Sugar Solution

| | Membrane type | Material | Molecular weight cutoff | Glucose | Xylose | Formic acid | Acetic acid | HMF | Furfural | Coumaric acid | Ferulic acid | Unit [g/L] 2,3-Dihydro-benzofuran |
|---|---|---|---|---|---|---|---|---|---|---|---|---|
| Example 1 (Fermentation test A) | NTR-7450 | s-PES | 600 to 800 | 73 | 30 | 0.1 | 2.4 | 0.12 | 0.75 | 0.2 | 0.09 | 0.015 |
| Example 1 | NTR-7410 | s-PES | 1000 | 65 | 25 | 0.1 | 2.4 | 0.12 | 0.75 | 0.18 | 0.08 | 0.01 |
| Example 1 (Fermentation test B) | SPE1 (Synder) | PES | 1000 | 66 | 25 | 0.1 | 2.4 | 0.12 | 0.75 | 0.18 | 0.08 | 0.01 |
| Example 1 | GH (GE) | PEG | 1000 | 65 | 25 | 0.1 | 2.4 | 0.12 | 0.75 | 0.2 | 0.085 | 0.012 |
| Example 1 (Fermentation test C) | GR95Pp (Alfa) | PES | 2000 | 50 | 20 | 0.1 | 2.4 | 0.12 | 0.75 | 0.15 | 0.075 | 0.01 |
| Example 1 | GK (GE) | PEG | 2000 | 48 | 20 | 0.1 | 2.4 | 0.12 | 0.75 | 0.18 | 0.08 | 0.01 |
| Comparative Example 1 | SPE3 (Synder) | PES | 3000 | 27 | 12 | 0.1 | 2.4 | 0.12 | 0.75 | 0.15 | 0.075 | 0.01 |
| Comparative Example 1 (Fermentation test D) | UTC-60 | PPA | Less than 600 (NF membrane) | 75 | 35 | 0.1 | 2.6 | 0.13 | 0.78 | 0.45 | 0.235 | 0.025 |
| Comparative Example 1 | HL | Composite membrane | Less than 600 (NF membrane) | 74 | 33 | 0.1 | 2.4 | 0.12 | 0.765 | 0.43 | 0.23 | 0.025 |
| Comparative Example 1 | DK | Composite membrane | Less than 600 (NF membrane) | 75 | 36 | 0.1 | 2.8 | 0.15 | 0.82 | 0.45 | 0.235 | 0.025 |

TABLE 15

Filtration Treatment of Steam-explosion-treated Aqueous Sugar Solution

Unit [g/L]

| | Membrane type | Material | Molecular weight cutoff | Glucose | Xylose | Formic acid | Acetic acid | HMF | Furfural | Coumaric acid | Ferulic acid | 2,3-Dihydro-benzofuran |
|---|---|---|---|---|---|---|---|---|---|---|---|---|
| Example 2 (Fermentation test E) | NTR-7450 | s-PES | 600 to 800 | 98 | 10 | 1.7 | 2.3 | 0.28 | 0.22 | 0.04 | 0.025 | 0.008 |
| Example 2 | NTR-7410 | s-PES | 1000 to 2000 | 90 | 8 | 1.7 | 2.3 | 0.28 | 0.22 | 0.03 | 0.023 | 0.008 |
| Example 2 (Fermentation test F) | SPE1 (Synder) | PES | 1000 | 92 | 9 | 1.7 | 2.3 | 0.28 | 0.22 | 0.03 | 0.022 | 0.008 |
| Example 2 | GH (GE) | PEG | 1000 | 90 | 8 | 1.7 | 2.3 | 0.28 | 0.22 | 0.03 | 0.022 | 0.008 |
| Example 2 (Fermentation test G) | GR95Pp (Alfa) | PES | 2000 | 84 | 7 | 1.7 | 2.3 | 0.28 | 0.22 | 0.03 | 0.022 | 0.008 |
| Example 2 | GK (GE) | PEG | 2000 | 80 | 7 | 1.7 | 2.3 | 0.28 | 0.22 | 0.03 | 0.022 | 0.008 |
| Comparative Example 2 | SPE3 (Synder) | PES | 3000 | 40 | 5 | 1.7 | 2.3 | 0.28 | 0.22 | 0.03 | 0.022 | 0.008 |
| Comparative Example 2 (Fermentation test H) | UTC-60 | PPA | Less than 600 (NF membrane) | 102 | 14 | 1.7 | 2.4 | 0.29 | 0.22 | 0.08 | 0.062 | 0.024 |
| Comparative Example 2 | HL | Composite membrane | Less than 600 (NF membrane) | 100 | 14 | 1.7 | 2.3 | 0.28 | 0.22 | 0.07 | 0.06 | 0.022 |
| Comparative Example 2 | DK | Composite membrane | Less than 600 (NF membrane) | 102 | 15 | 1.7 | 2.6 | 0.31 | 0.24 | 0.08 | 0.064 | 0.024 |

Example 3

The same concentration test as in Example 1 was carried out for the permeate obtained by filtration of the ammonia-treated aqueous sugar solution described in Reference Example 5 through the microfiltration membrane. The results are shown in Table 16.

Comparative Example 3

The permeate obtained by filtration of the ammonia-treated aqueous sugar solution through the microfiltration membrane was subjected to filtration treatment using the same membranes as in Comparative Example 1. The results on the liquid composition are shown in Table 16. Similarly to the results of comparison between Example 1 and Comparative Example 1, use of the ultrafiltration membrane with a molecular weight cutoff of 3,000 resulted in an extreme decrease in the rate of concentration of monosaccharides. In terms of concentration with the nanofiltration membranes, coumaric acid, ferulic acid and 2,3-dihydrobenzofuran were concentrated, although the concentration of the concentrate somewhat varied.

TABLE 16

Filtration Treatment of Ammonia-treated Aqueous Sugar Solution

Unit [g/L]

| | Membrane type | Material | Molecular weight cutoff | Glucose | Xylose | Formic acid | Acetic acid | HMF | Furfural | Coumaric acid | Ferulic acid | 2,3-Dihydro-benzofuran |
|---|---|---|---|---|---|---|---|---|---|---|---|---|
| Example 3 | NTR-7450 | s-PES | 600 to 800 | 110 | 58 | 1.1 | 0.5 | 0.012 | 0.004 | 0.04 | 0.008 | 0.005 |
| Example 3 | NTR-7410 | s-PES | 1000 to 2000 | 106 | 52 | 1.1 | 0.5 | 0.012 | 0.004 | 0.03 | 0.008 | 0.005 |
| Example 3 | SPE1 (Synder) | PES | 1000 | 105 | 51 | 1.1 | 0.5 | 0.012 | 0.004 | 0.03 | 0.008 | 0.005 |
| Example 3 | GH (GE) | PEG | 1000 | 100 | 48 | 1.1 | 0.5 | 0.012 | 0.004 | 0.03 | 0.008 | 0.005 |
| Example 3 | GR95Pp (Alfa) | PES | 2000 | 82 | 42 | 1.1 | 0.5 | 0.012 | 0.004 | 0.03 | 0.008 | 0.005 |
| Example 3 | GK (GE) | PEG | 2000 | 80 | 40 | 1.1 | 0.5 | 0.012 | 0.004 | 0.03 | 0.008 | 0.005 |
| Comparative Example 3 | SPE3 (Synder) | PES | 3000 | 60 | 30 | 1.1 | 0.5 | 0.012 | 0.004 | 0.03 | 0.008 | 0.005 |
| Comparative Example 3 | UTC-60 | PPA | Less than 600 (NF membrane) | 119 | 70 | 1.1 | 0.6 | 0.014 | 0.005 | 0.088 | 0.024 | 0.007 |
| Comparative Example 3 | HL | Composite membrane | Less than 600 (NF membrane) | 118 | 68 | 1.1 | 0.5 | 0.013 | 0.005 | 0.078 | 0.022 | 0.006 |
| Comparative Example 3 | DK | Composite membrane | Less than 600 (NF membrane) | 120 | 71 | 1.1 | 0.6 | 0.015 | 0.005 | 0.089 | 0.024 | 0.008 |

Example 4

Figure 3:
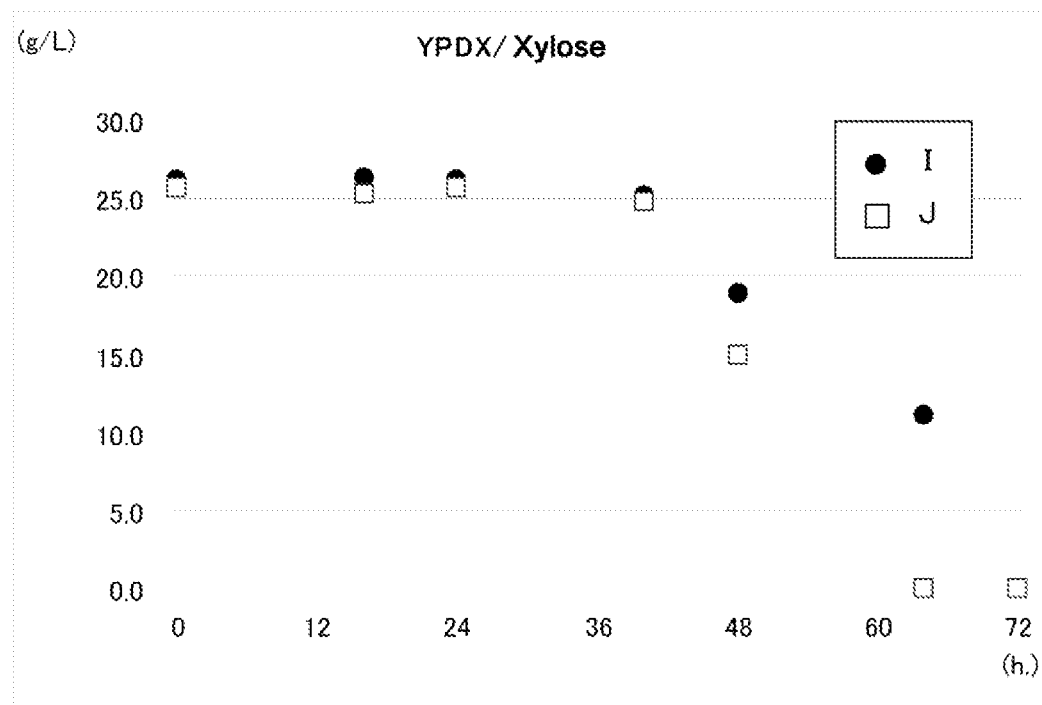
FIG. 3 shows the results of improvement of fermentability by subjecting a cellulose-containing biomass to hydrothermal treatment to obtain an aqueous sugar solution, filtering the resulting solution through an ultrafiltration membrane, and then subjecting the obtained permeate to membrane concentration, which fermentability was evaluated using as an index the xylose consumption rate.

A comparison was made between the case where, before the filtration treatment of the hydrothermally treated aqueous sugar solution prepared in Reference Example 6 using the ultrafiltration membrane "NTR-7450" or "NTR-7410", filtration treatment was carried out using as the second ultrafiltration membrane an ultrafiltration membrane having a molecular weight cutoff of 10,000 (manufactured by Applied Membranes, Inc.; material: polyethersulfone), and the case where the filtration treatment using the second ultrafiltration membrane was not carried out. The results are shown in Table 17. We found that, in the cases where the treatment with the second ultrafiltration membrane was carried out, the membrane permeation flux during the ultrafiltration membrane treatment with "NTR-7450" or "NTR-7410" (in terms of the average over the processing time) largely increased, and the concentration rate of monosaccharides in the feed side was improved.

concentrate, reagents were added such that the composition shown in Table 20 was attained. The same fermentation test as in Reference Example 7 was carried out, and the xylose consumption rate was measured. The results are shown in FIG. 3 (see J in FIG. 3).

Comparative Example 4

Table 19 shows the compositions of fermentation inhibitors and monosaccharides in 0.75 L of the concentrate in the feed side obtained by filtration treatment, using a nanofiltration membrane "UTC-60", of 1.5 L of the permeate obtained by filtration of the hydrothermally treated aqueous sugar solution prepared in Reference Example 6 through a microfiltration membrane. In the same manner as in Example 5, reagents were added to this concentrate such that the composition shown in Table 20 was attained, and the resulting mix-

TABLE 17

Comparison among Compositions of Concentrates Prepared with or without Second Ultrafiltration Membrane Treatment

| | Membrane type | Membrane pretreatment | Permeation flux | Glucose | Xylose | Formic Acid | Acetic acid | HMF | Furfural | Coumaric acid | Ferulic acid | Unit [g/L] 2,3-Dihydro-benzofuran |
|---|---|---|---|---|---|---|---|---|---|---|---|---|
| Example 4 | NTR-7450 | No | 0.5 m/D | 18 | 30 | 1.1 | 2.2 | 0.12 | 0.48 | 0.22 | 0.15 | 0.03 |
| Example 4 | NTR-7450 | Yes | 1.5 m/D | 21 | 40 | 1.2 | 2.4 | 0.15 | 0.5 | 0.23 | 0.15 | 0.03 |
| Example 4 | NTR-7410 | No | 0.64 m/D | 14 | 25 | 1.1 | 2.2 | 0.12 | 0.47 | 0.19 | 0.13 | 0.03 |
| Example 4 | NTR-7410 | Yes | 2.0 m/D | 17 | 30 | 1.1 | 2.3 | 0.13 | 0.48 | 0.2 | 0.13 | 0.03 |

Example 5

In the same manner as in Example 1, 1.5 L of the permeate obtained by filtration of the hydrothermally treated aqueous sugar solution prepared in Reference Example 6 through a microfiltration membrane was subjected to filtration treatment using an ultrafiltration membrane "NTR-7410" (manufactured by Nitto Denko Corporation; material: sulfonated polyethersulfone; molecular weight cutoff: 1,000). The compositions of fermentation inhibitors and monosaccharides in the concentrate in the feed side (0.5 L) and the filtrate in the permeate side (1.0 L) obtained are shown in Table 18. Thereafter, the filtrate was filtered through a nanofiltration membrane "UTC-60" (manufactured by Toray Industries, Inc.; material: piperazine polyamide). The compositions of fermentation inhibitors and monosaccharides in the concentrate in the feed side (0.33 L) are shown in Table 19. To this ture was subjected to a fermentation test. The results (xylose consumption rates) were as shown in FIG. 3 (see J in FIG. 3).

We found that, although the sugar liquid obtained in Example 5 contained somewhat higher concentrations of coumaric acid, ferulic acid and 2,3-dihydrobenzofuran, the fermentability of the sugar liquid was better than in Comparative Example 4 in terms of the xylose consumption rate. This was assumed to be due to the presence, in the aqueous sugar solution, of unidentified fermentation inhibitors to which an ultrafiltration membrane having a molecular weight cutoff of 600 to 2,000 is impermeable. Further, from Example 5, it was found that not only the sugar liquid in the feed side of the ultrafiltration membrane having a molecular weight cutoff of 600 to 2,000, but also the second concentrated sugar liquid obtained by filtering the filtrate in the permeate side through a nanofiltration membrane and/or reverse osmosis membrane and collecting the sugar liquid from the feed side, are sugar liquids having good fermentability.

TABLE 18

Compositions of Concentrated Hydrothermally Treated Liquid and Filtrate Obtained with Ultrafiltration Membrane

| | Membrane type | Liquid subjected to treatment | Glucose | Xylose | Formic acid | Acetic acid | HMF | Furfural | Coumaric acid | Ferulic acid | Unit [g/L] 2,3-Dihydro-benzofuran |
|---|---|---|---|---|---|---|---|---|---|---|---|
| Example 5 | NTR-7410 | Concentrate | 14 | 25 | 1.1 | 2.2 | 0.12 | 0.47 | 0.2 | 0.13 | 0.03 |
| Example 5 | NTR-7410 | Filtrate | 3.5 | 10 | 1.1 | 2.2 | 0.12 | 0.51 | 0.18 | 0.11 | 0.03 |

TABLE 19

Comparison between Concentrate obtained by Nanofiltration Membrane Treatment of Raw Hydrothermally Treated Liquid and Concentrate Obtained by Ultrafiltration Membrane Treatment of Raw Hydrothermally Treated Liquid followed by Nanofiltration Membrane Treatment of Resulting Filtrate Unit [g/L]

| | Membrane type | Liquid subjected to treatment | Concentration rate | Glucose | Xylose | Formic acid | Acetic acid | HMF | Furfural | Coumaric acid | Ferulic acid | 2,3-Dihydro-benzofuran |
|---|---|---|---|---|---|---|---|---|---|---|---|---|
| Comparative Example 4 (fermentation test I) | UTC-60 | Raw liquid | 2-fold | 14 | 30 | 1.1 | 2.4 | 0.12 | 0.49 | 0.4 | 0.26 | 0.06 |
| Example 5 (fermentation test J) | UTC-60 | Raw filtrate material | 3-fold | 10 | 30 | 1.1 | 2.5 | 0.12 | 0.5 | 0.54 | 0.33 | 0.09 |

TABLE 20

| Composition | Concentration of composition |
|---|---|
| Glucose | 15 g/L |
| Xylose | 25 g/L |
| Bacto Yeast Extract | 10 g/L |
| Peptone | 20 g/L |

Reference Example 8

Evaluation of Capacities to Remove Fermentation Inhibitors from Aqueous Sugar Solution at Different pHs Using the hydrothermally treated liquid described in Reference Example 6 after adjusting the pH to various values, the permeation rates of fermentation inhibitors contained in the aqueous sugar solution through an ultrafiltration membrane were compared and studied. The permeation rate of each fermentation inhibitor was represented as the ratio (%) calculated by dividing the concentration of the component in the filtrate side by the concentration of the component in the feed side in the membrane treatment and multiplying the resulting value by 100. Since addition of dilute sulfuric acid or sodium hydroxide to the hydrothermally treated liquid causes production of precipitates, centrifugation and subsequent microfiltration membrane treatment were carried out thereafter. Thereafter, an ultrafiltration membrane "NTR-7410" (manufactured by Nitto Denko Corporation; material: sulfonated polyethersulfone; molecular weight cutoff: 1,000) was placed in a flat membrane filtration unit "SEPA-II" (manufactured by GE Osmonics), and filtration treatment was carried out at a membrane surface linear velocity of 20 cm/second at a filtration pressure of 2 MPa. Since the concentration in the filtrate side does not become stable in a short time, the filtrate obtained by 20 minutes of filtration was returned to the feed side, and stable filtrate was sampled 20 minutes later. As a result of calculation of the permeation rates, we found as shown in Table 21 that, by adjusting the pH to not more than 5, the performance for removal of coumaric acid and ferulic acid, which are aromatic fermentation inhibitors having a carboxylic group, largely increases.

TABLE 21

Permeation Rates of Aqueous Sugar Solution (Hydrothermally Treated Liquid) through Ultrafiltration Membrane at Different pHs (Unit: %)

| | Glucose | Xylose | Formic acid | Acetic acid | HMF | Furfural | Coumaric acid | Ferulic acid | 2,3-Dihydrobenzofuran |
|---|---|---|---|---|---|---|---|---|---|
| pH 3 | 9 | 30 | 110 | 105 | 100 | 105 | 100 | 100 | 95 |
| pH 4 | 15 | 37 | 110 | 105 | 100 | 110 | 89 | 75 | 95 |
| pH 5 | 17 | 42 | 100 | 100 | 102 | 110 | 68 | 49 | 100 |
| pH 6 | 18 | 45 | 90 | 84 | 104 | 110 | 15 | 7 | 100 |
| pH 7 | 17 | 43 | 88 | 80 | 110 | 115 | 10 | 5 | 100 |
| pH 9 | 17 | 46 | 85 | 78 | 105 | 115 | 10 | 5 | 100 |

Example 6

Figure 4:
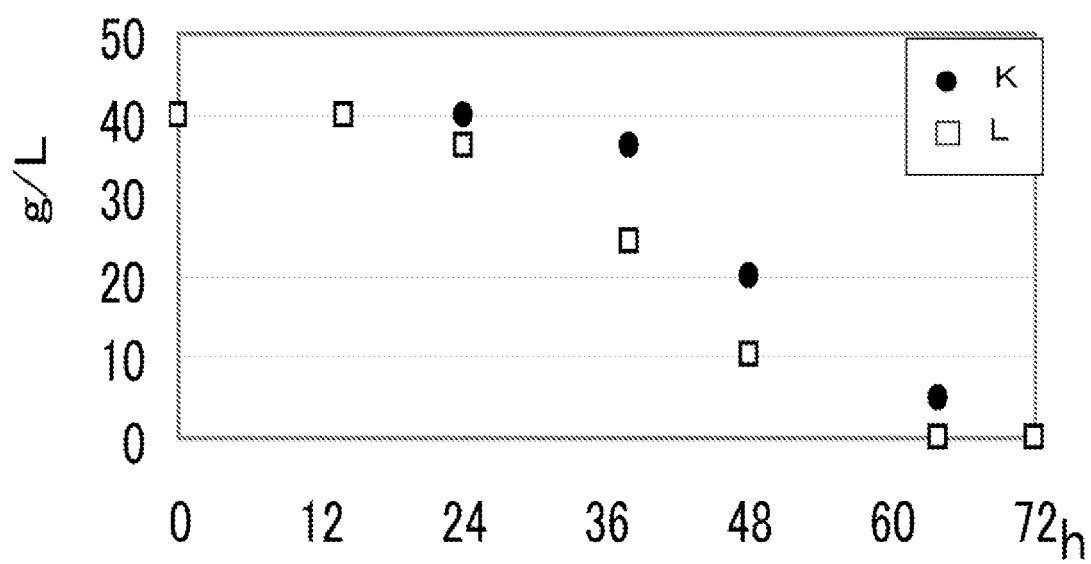
FIG. 4 shows the results of improvement of fermentability by subjecting a cellulose-containing biomass to dilute sulfuric acid treatment to obtain an aqueous sulfuric acid solution, filtering the resulting solution through an ultrafiltration membrane, and then subjecting the obtained permeate to membrane concentration, which fermentability was evaluated using as an index the xylose consumption rate.

The aqueous sulfuric acid solution obtained in Reference Example 3 was neutralized to pH 4.0 with ammonia, and subjected to microfiltration membrane treatment. In the same manner as in Example 1, 1.5 L of the obtained permeate was filtered through an ultrafiltration membrane "NTR-7450" (manufactured by Nitto Denko Corporation; material: sulfonated polyethersulfone; molecular weight cutoff: 600 to 800). The compositions of fermentation inhibitors and monosaccharides contained in the concentrate in the feed side (0.5 L) and the filtrate in the permeate side (1.0 L) were as shown in Table 22. The filtrate was filtered through a nanofiltration membrane "UTC-60" (manufactured by Toray Industries, Inc.; material: piperazine polyamide). The compositions of fermentation inhibitors and monosaccharides in the concentrate in the feed side (0.33 L) are shown in Table 23. Reagents were added to this concentrate such that the composition shown in Table 24 was attained, and the resulting mixture was subjected to the same fermentation test as in Reference Example 7. The results of measurement of the xylose consumption rate are shown in FIG. 4 (see L in FIG. 4).

Comparative Example 5

The aqueous sulfuric acid solution obtained in Reference Example 3 was neutralized to pH 4.0 with ammonia, and subjected to microfiltration membrane treatment. Filtration treatment of 1.5 L of the obtained permeate was carried out with a nanofiltration membrane "UTC-60". The compositions of fermentation inhibitors and monosaccharides contained in 0.75 L of the concentrate in the feed side were as shown in Table 22. In the same manner as in Example 6, reagents were added to this concentrate such that the composition shown in Table 24 was attained, and the resulting mixture was subjected to a fermentation test. The results (xylose consumption rates) are shown in FIG. 4 (see K in FIG. 4).

We found that, although the sugar liquid obtained in Example 6 contained somewhat higher concentrations of coumaric acid, ferulic acid and 2,3-dihydrobenzofuran, the sugar liquid had higher fermentability than that of Comparative Example 5 in terms of the xylose consumption rate. This was assumed to be due to the presence, in the aqueous sugar solution, of unidentified fermentation inhibitors to which an ultrafiltration membrane having a molecular weight cutoff of 600 to 2,000 is impermeable. Further, from Example 6, it was found that not only the sugar liquid in the feed side of the ultrafiltration membrane having a molecular weight cutoff of 600 to 2,000, but also the second concentrated sugar liquid obtained by filtering the filtrate in the permeate side through a nanofiltration membrane and/or reverse osmosis membrane and collecting the sugar liquid from the feed side, are sugar liquids having good fermentability.

TABLE 22

Compositions of concentrate and filtrate obtained by ultrafiltration membrane treatment of aqueous sulfuric acid solution

| | Membrane type | Liquid subjected to treatment | Glucose | Xylose | Formic acid | Acetic acid | HMF | Furfural | Coumaric acid | Ferulic acid | Unit [g/L] 2,3-Dihydro-benzofuran |
|---|---|---|---|---|---|---|---|---|---|---|---|
| Example 6 | NTR-7450 | Concentrate | 5 | 36 | 0.6 | 3.4 | 0.08 | 0.2 | 0.15 | 0.1 | 0.03 |
| Example 6 | NTR-7450 | Filtrate | 1 | 12 | 0.6 | 3.4 | 0.08 | 0.2 | 0.13 | 0.09 | 0.03 |

TABLE 23

Comparison between Concentrate obtained by Nanofiltration Membrane Treatment of Raw Aqueous Sulfuric Acid Solution and Concentrate Obtained by Ultrafiltration Membrane Treatment of Raw Aqueous Sulfuric Acid Solution followed by Nanofiltration Membrane Treatment of Resulting Filtrate

| | Membrane type | Liquid subjected to treatment | Concentration rate | Glucose | Xylose | Formic acid | Acetic acid | HMF | Furfural | Coumaric acid | Ferulic acid | Unit [g/L] 2,3-Dihydro-benzofuran |
|---|---|---|---|---|---|---|---|---|---|---|---|---|
| Comparative Example 5 (Fermentation test K) | UTC-60 | Raw liquid | 2-fold | 6 | 40 | 0.6 | 3.4 | 0.08 | 0.2 | 0.15 | 0.1 | 0.03 |
| Example 6 (Fermentation test L) | UTC-60 | Raw filtrate material | 3.3-fold | 2.7 | 40 | 0.7 | 3.6 | 0.1 | 0.25 | 0.16 | 0.11 | 0.04 |

TABLE 24

| Composition | Concentration of composition |
|---|---|
| Glucose | 6 g/L |
| Xylose | 40 g/L |
| Bacto Yeast Extract | 10 g/L |
| Peptone | 20 g/L |
| pH | 6.5 |

Industrial Applicability

Fermentation inhibitors can be efficiently removed from an aqueous sugar solution derived from a cellulose-containing biomass, and, on the other hand, a purified sugar liquid containing monosaccharides such as glucose and xylose can be produced at high purity and at high yield so that use of the purified sugar liquid as a fermentation feedstock enables enhancement of the efficiencies of fermentative production of various chemical products.

The invention claimed is:

1. A method of producing a sugar liquid from a cellulose-containing biomass as a raw material comprising:
   (1) hydrolyzing the cellulose-containing biomass to produce an aqueous sugar solution; and
   (2) filtering said aqueous sugar solution obtained in (1) through an ultrafiltration membrane having a molecular weight cutoff of 600 to 2,000 to move one or more fermentation inhibitors into the permeate side and collect the sugar liquid from the feed side.

2. The method according to claim 1, wherein said fermentation inhibitor(s) comprise(s) one or more substances selected from the group consisting of coumaric acid, ferulic acid and 2,3-dihydrobenzofuran.

3. The method according to claim 1, wherein, in (2), said aqueous sugar solution is filtered after adjusting the pH to not more than 5.

4. The method according to claim 1, wherein the material of the functional layer of said ultrafiltration membrane used in (2) is polyethersulfone.

5. The method according to claim 1, comprising filtering the permeate obtained in step (2) containing the sugar liquid and/or fermentation inhibitor through a nanofiltration membrane and/or reverse osmosis membrane, to collect a concentrated sugar liquid from the feed side.

6. The method according to claim 2, wherein, in (2), said aqueous sugar solution is filtered after adjusting the pH to not more than 5.

7. The method according to claim 2, wherein the material of the functional layer of said ultrafiltration membrane used in (2) is polyethersulfone.

8. The method according to claim 3, wherein the material of the functional layer of said ultrafiltration membrane used in (2) is polyethersulfone.

9. The method according to claim 1, comprising filtering the permeate obtained in step (2) containing the sugar liquid and/or fermentation inhibitor through a nanofiltration membrane and/or reverse osmosis membrane, to collect a concentrated sugar liquid from the feed side, wherein the one or more fermentation inhibitors comprise one or more substances selected from the group consisting of coumaric acid, ferulic acid and 2,3-dihydrobenzofuran.

10. The method according to claim 1, comprising:
a) after step (1) adjusting the pH to not more than 5; and
b) after step (2) filtering the permeate obtained in step (2) containing the sugar liquid and/or fermentation inhibitor through a nanofiltration membrane and/or reverse osmosis membrane, to collect a concentrated sugar liquid from the feed side.

11. The method according to claim 1, comprising filtering the permeate obtained in step (2) containing the sugar liquid and/or fermentation inhibitor through a nanofiltration membrane and/or reverse osmosis membrane, to collect a concentrated sugar liquid from the feed side, wherein the material of the functional layer of the ultrafiltration membrane used in step (2) is polyethersulfone.

* * * * *